United States Patent
Thienphrapa et al.

(10) Patent No.: US 11,564,748 B2
(45) Date of Patent: Jan. 31, 2023

(54) REGISTRATION OF A SURGICAL IMAGE ACQUISITION DEVICE USING CONTOUR SIGNATURES

(71) Applicant: KONINKLIJKE PHILIPS N.V., Eindhoven (NL)

(72) Inventors: Paul Thienphrapa, Cambridge, MA (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1162 days.

(21) Appl. No.: 16/066,000

(22) PCT Filed: Dec. 27, 2016

(86) PCT No.: PCT/EP2016/082704
§ 371 (c)(1),
(2) Date: Jun. 25, 2018

(87) PCT Pub. No.: WO2017/114828
PCT Pub. Date: Jul. 6, 2017

(65) Prior Publication Data
US 2019/0008592 A1  Jan. 10, 2019

Related U.S. Application Data

(60) Provisional application No. 62/272,493, filed on Dec. 29, 2015.

(51) Int. Cl.
*A61B 5/05* (2021.01)
*A61B 34/20* (2016.01)
(Continued)

(52) U.S. Cl.
CPC ............ *A61B 34/20* (2016.02); *A61B 1/0005* (2013.01); *A61B 1/00039* (2013.01);
(Continued)

(58) Field of Classification Search
IPC .................. A61B 34/20,2034/2057, 2034/2065
See application file for complete search history.

(56) References Cited

U.S. PATENT DOCUMENTS

2005/0272991 A1* 12/2005 Xu ........................ A61B 6/032
600/407
2010/0091035 A1   4/2010 Kirchberg
(Continued)

FOREIGN PATENT DOCUMENTS

WO   2009109874 A1   9/2009
WO   2011031134      3/2011

*Primary Examiner* — Joel F Brutus

(57) ABSTRACT

Registration of a surgical image acquisition device (e.g. an endoscope) using preoperative and live contour signatures of an anatomical object is described. A control unit includes a processor configured to compare the real-time contour signature to the database of preoperative contour signatures of the anatomical object to generate a group of potential contour signature matches for selection of a final contour match. Registration of an image acquisition device to the surgical site is realized based upon an orientation corresponding to the selected final contour signature match.

23 Claims, 5 Drawing Sheets

(51) Int. Cl.
*G06T 7/73* (2017.01)
*G06V 10/75* (2022.01)
*A61B 1/00* (2006.01)
*A61B 1/04* (2006.01)
*G06T 19/00* (2011.01)
*A61B 90/00* (2016.01)
*A61B 90/30* (2016.01)

(52) U.S. Cl.
CPC ............ *A61B 1/00048* (2013.01); *A61B 1/04* (2013.01); *G06T 7/74* (2017.01); *G06T 19/006* (2013.01); *G06V 10/752* (2022.01); *A61B 2034/2057* (2016.02); *A61B 2034/2065* (2016.02); *A61B 2090/306* (2016.02); *A61B 2090/364* (2016.02); *A61B 2090/3614* (2016.02); *G06T 2207/10068* (2013.01); *G06T 2207/10072* (2013.01); *G06T 2207/20108* (2013.01); *G06T 2207/30004* (2013.01); *G06T 2207/30244* (2013.01); *G06T 2219/2004* (2013.01)

(56) References Cited

U.S. PATENT DOCUMENTS

| | | |
|---|---|---|
| 2011/0054300 A1 | 3/2011 | Yamamoto |
| 2014/0051986 A1* | 2/2014 | Zhao .......................... G06T 7/33 600/424 |
| 2014/0301618 A1 | 10/2014 | Popovic |

* cited by examiner

REGISTRATION OF A SURGICAL IMAGE ACQUISITION DEVICE USING CONTOUR SIGNATURES

CROSS-REFERENCE TO PRIOR APPLICATIONS

This application is the U.S. National Phase application under 35 U.S.C. § 371 of International Application No. PCT/EP2016/082704, filed on Dec. 27, 2016, which claims the benefit of U.S. Provisional Patent Application No. 62/272,493, filed on Dec. 29, 2015. These applications are hereby incorporated by reference herein.

BACKGROUND

A surgical image acquisition device, such as an endoscope, comprises a thin, elongated camera assembly that allows clinician to view the internal anatomy of a patient without the need to surgically expose the anatomy for a direct view. Endoscopes can fit through narrow natural orifices or small incisions in the skin, thus resulting in reduced trauma to the patient as compared to visualization and intervention without the aid of an endoscope.

Registration of the endoscope to with some desired frame of reference enables capabilities such as registration of preoperative images to the live endoscope feed, which can help with localization of anatomical targets and lesions. The preoperative images may include 3D images such as those obtained via computed tomography (CT), ultrasound, magnetic resonance imaging (MRI), positron emission tomography (PET), single-photon emission computed tomography (SPECT).

A variety of current methods exist to register an endoscope to the workspace in its view. One class of approaches uses external localization systems such as optical and electromagnetic tracking, which has the advantage of using mature, commercially available technology, but also entails additional hardware, workspace and workflow complexity.

Alternatively, registration can be performed by matching features visible in the live endoscopic view with corresponding features known through other ways such as a preoperative CT. The features can be manually selected by the user which introduces workflow issues and user-error. The features can be selected by automated image processing algorithms known in art. Such an image-based registration method is streamlined from the user point of view, though is less technologically mature due to sensitivity to the imaged scene. What is needed, therefore, is a system and apparatus that overcomes at least the shortcomings described above

SUMMARY

In accordance with a representative embodiment, a control unit for registration of an image acquisition device is configured to acquire a live image of an anatomical object at a surgical site. The control unit comprises a processor configured to: receive preoperative images of the anatomical object from one or more orientations, and generate a database of preoperative contour signatures of the anatomical object; generate a real-time contour signature of the anatomical object from the acquired live image; compare the real-time contour signature to the database of preoperative contour signatures of the anatomical object to generate a group of potential contour signature matches for selection of a final contour match; and register the image acquisition device to the surgical site based upon an orientation corresponding to the selected final contour signature match.

In accordance with another representative embodiment, a surgical system comprising an image acquisition device is configured to acquire a live image of an anatomical object at a surgical site, and a display configured to display live images of the surgical site, and a control unit. The control unit comprises input/output (I/O) circuitry configured to receive the acquired live image from the image acquisition device, receive preoperative images of the anatomical object from an image acquisition device, and provide potential contour signature matches of the anatomical object to at least one display. A processor is configured to: generate a database of preoperative contour signatures of the anatomical object from the preoperative images of the anatomical object from one or more orientations; generate a real-time contour signature of the anatomical object from the acquired live image; compare the real-time contour signature to the database of preoperative contour signatures of the anatomical object to generate a group of potential contour signature matches; transmit the real-time contour signature and the group of potential contour signature matches to the display for selection of a final contour signature match by a user; and register the image acquisition device to the surgical site based upon an orientation corresponding to the selected final contour signature match.

In accordance with another representative embodiment, a non-transitory computer-readable storage medium, having stored therein machine readable instructions, is configured to be executed by a processor to control a surgical system including an image acquisition device configured to acquire a live image of an anatomical object at a surgical site, the machine readable instructions being configured to perform a method to register the image acquisition device to the surgical site. The method comprises: generating a database of preoperative contour signatures of the anatomical object from preoperative images of the anatomical object over a range of three-dimensional (3D) orientations; generating a real-time contour signature of the anatomical object from the acquired live image; comparing the real-time contour signature to the database of preoperative contour signatures of the anatomical object to generate a group of potential contour signature matches for selection of a final contour signature match; and registering the image acquisition device to the surgical site based upon an orientation corresponding to the selected final contour signature match.

BRIEF DESCRIPTION OF THE DRAWINGS

The representative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
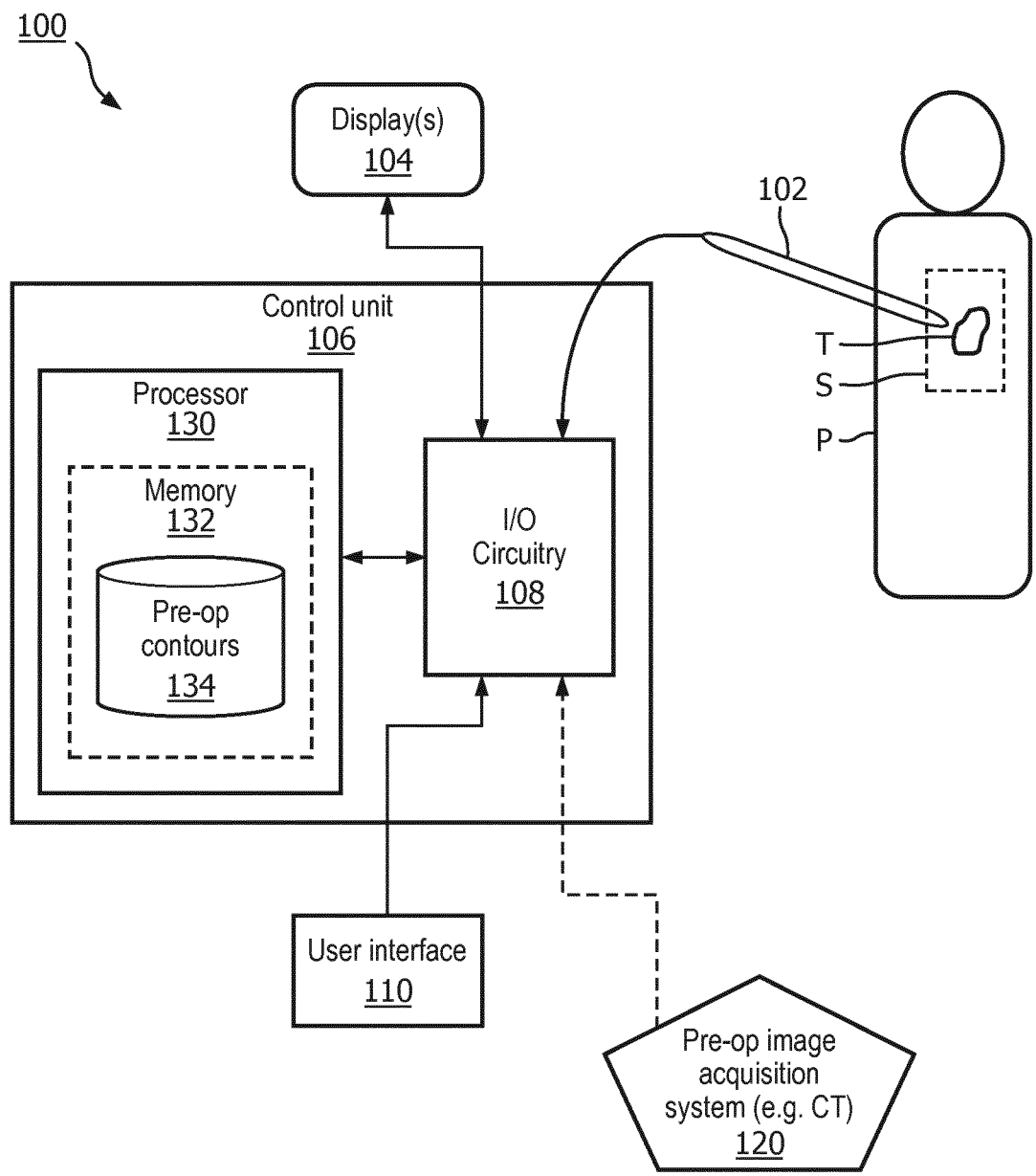
FIG. 1 is a schematic block diagram illustrating a surgical system using preoperative and intraoperative (or live) contour signatures of an anatomical object for registration of a surgical image acquisition device in accordance with features of an embodiment of the present invention.

In the following detailed description, for purposes of explanation and not limitation, representative embodiments disclosing specific details are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the present teachings.

It is to be understood that the terminology used herein is for purposes of describing particular embodiments only, and is not intended to be limiting. Any defined terms are in addition to the technical and scientific meanings of the defined terms as commonly understood and accepted in the technical field of the present teachings.

As used in the specification and appended claims, the terms 'a', 'an' and 'the' comprises both singular and plural referents, unless the context clearly dictates otherwise. Thus, for example, 'a device' includes one device and plural devices.

As used herein, the statement that two or more parts or components are "coupled" shall mean that the parts are joined or operate together either directly or indirectly, i.e., through one or more intermediate parts or components, so long as a link occurs.

Directional terms/phrases and relative terms/phrases may be used to describe the various elements' relationships to one another, as illustrated in the accompanying drawings. These terms/phrases are intended to encompass different orientations of the device and/or elements in addition to the orientation depicted in the drawings.

Relative terms, such as "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be "below" that element. Similarly, if the device were rotated by 90° with respect to the view in the drawings, an element described "above" or "below" another element would now be "adjacent" to the other element; where "adjacent" means either abutting the other element, or having one or more layers, materials, structures, etc., between the elements.

As used in the specification and appended claims, and in addition to their ordinary meanings, the terms 'substantial' or 'substantially' mean to with acceptable limits or degree. For example, 'substantially cancelled' means that one skilled in the art would consider the cancellation to be acceptable.

The present teachings relate generally to matching the contours or outlines of anatomical objects to corresponding contours. The systems, apparatuses and methods of the present teachings are useful in registering comparatively sparse visual features, such as organs in abdominal area (kidneys, livers, and bladders). As will become clearer as the present description continues, representative embodiments are directed to apparatuses, systems, methods, and non-transitory computer-readable medium for registration of a surgical image acquisition device using preoperative and interoperative (real-time) contour signatures of an anatomical object.

Initially, it is noted that organs such as the kidneys and liver, for example, are less textured than organs such as the heart, making the use of visible surface features for registration challenging. In such cases, a beneficial aspect of the present teachings may be to match the contour of such organs that otherwise lack visually detectable features. Contours may be delineated manually or automatically, and may be complete or partial contours of an organ. Because the view of an organ at a particular orientation often has a unique shape relative to other organs and orientations, its contour or 3D contour can be reduced to a compact, lower-dimension signature for fast real-time matching and registration.

Referring initially to FIGS. 1 and 2, a surgical system 100 in accordance with features of the present teachings will be described. In particular, surgical system 100 may be used for many different medical and surgical procedures including, but are not limited to, minimally invasive cardiac surgery (e.g., coronary artery bypass grafting or mitral valve replacement), minimally invasive abdominal surgery (laparoscopy) (e.g., prostatectomy or cholecystectomy), and natural orifice translumenal endoscopic surgery. It is emphasized that the noted medical and surgical procedures are merely illustrative, and that other surgical procedures within the purview of one of ordinary skill in the art having had the benefit of the present disclosure are contemplated.

FIG. 1 schematically illustrates the surgical system 100 including an image acquisition device 102 configured to acquire a live image or live images of an anatomical object (e.g. an organ) or target T at a surgical site S, a display 104, and a control unit 106.

The image acquisition device 102 is configured to acquire a live image or live images of an organ or other target T at the surgical site S. Generally, the term "endoscopic" is broadly defined herein as a characterization of images acquired by any type of endoscope having the ability to image from inside a body. Examples of an endoscope for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhino laryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, or miniaturized (e.g. CCD based) imaging systems. Further details of an endoscopic system contemplated for use in connection with the present teachings may be found, for example, in commonly-owned U.S. Patent Application 20140301618, the disclosure of which is specifically incorporated herein by reference.

In certain representative embodiments, the endoscope may include a rigid or flexible tube, a light delivery system to illuminate the organ or object under inspection (e.g. the light source is normally outside the body and the light is typically directed via an optical fiber system), a lens system transmitting the image from the objective lens to the viewer, typically a relay lens system in the case of rigid endoscopes or a bundle of fiberoptics in the case of a fiberscope. Also contemplated are videoscopes, with no eyepiece, in which a camera transmits images to a screen for image capture. An additional channel may allow entry of medical instruments or manipulators.

The display 104 is configured to provide one or more of a variety of images useful to the clinician during a surgical procedure. These images include, for example, real-time images from the image acquisition device 102, and preoperative images, as described more fully below.

The display 104 may include one or more displays that may be co-located near the surgeon or positioned adjacent to various elements of the surgical system 100. The display 104 comprises an output device, or a user interface, or both, adapted for displaying images or data, as described more fully herein. The display 104 may include one or more displays that may be co-located near the clinician positioned adjacent to various elements of the surgical system 100. The display 104 is configured to display live or preoperative images of the surgical site S.

A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

The control unit 106 is generally configured to provide one or more control commands to control the acquisition and processing of live and preoperative images related to the surgical site S and anatomical object or target T. The control unit 106 is configured to receive input from various components of the surgical system 100, and to provide outputs thereto, as is described more fully below. The control unit 106 comprises input/output (I/O) circuitry 108, which receives inputs from various components of the surgical system 100, and provides output to and receives inputs from a processor 130, as is described more fully below.

The processor 130 comprises a memory 132, which comprises a database 134 of preoperative contour signatures of the anatomical object T, data acquired from the image acquisition device 102, and machine readable instructions (programs) configured to be executed by the processor 130.

The preoperative images stored in memory may include 3D images such as those obtained via computed tomography (CT), ultrasound, magnetic resonance imaging (MRI), positron emission tomography (PET), single-photon emission computed tomography (SPECT) etc. The real-time images may include still or video images captured through medical imaging during an open surgery or minimally invasive procedure, such as images obtained by endoscopy, X-ray, ultrasound, single slice MRI, for example.

The processor 130 may comprise one or more microprocessors that may be programmed using software (e.g., microcode) to perform various functions discussed herein. Notably, the processor 130 may comprise more than one processor or processing core. The processor 130 may for instance be a multi-core processor. The processor 130 may also comprise a collection of processors within a single computer system (not shown) or distributed among multiple computer systems (not shown) associated with the surgical system 100. As will be appreciated as the present description continues, many programs have their instructions performed by the processor 130 that may be within the same computing device or which may even be distributed across multiple computing devices.

Examples of components that may be employed as the processor 130 in various embodiments of the present disclosure include, but are not limited to, conventional microprocessors, microcontrol units, application specific integrated circuits (ASICs), and field-programmable gate arrays (FPGAs).

The memory 132 is configured to store software useful to the processor, and various types of data gathered during the course of the function of the various components of the surgical system 100. These data include image data and tracking data gathered as described more fully below. The memory 132 may also store pre-operative data, such as pre-operative image data.

Furthermore, the memory 132 stores machine readable instructions configured to be executed by the processor 130 to control the surgical system 100. These instructions (programs) are encoded in the memory 132, and when executed on the processor 130, perform at least some of the functions discussed herein. (The terms "program" or "computer program" are used herein in a generic sense to refer to any type of computer code (e.g., software or microcode) that can be employed to program the control unit 106.) For example, and as described more fully herein, machine readable instructions stored in memory 132 are configured to be executed by the processor 130 to control the surgical system 100 including the image acquisition device 102 configured to acquire a live image of an anatomical object at a surgical site S. Furthermore, the machine readable instructions, through the processor 130, are configured to perform a method, which is described more fully below, to register the image acquisition device 102 to the surgical site S using both preoperative and interoperative images.

The memory 132 may comprise non-volatile computer memory, or volatile computer memory, or both, including, but not limited to: a floppy disk, a magnetic hard disk drive, a solid state hard disk, flash memory, a USB thumb drive, Random Access Memory (RAM), Read Only Memory (ROM), programmable read-only memory (PROM), electrically programmable read-only memory (EPROM), electrically erasable and programmable read only memory (EEPROM), universal serial bus (USB) drive, floppy disks, compact disks (CDs), optical disks, magnetic tape, etc.), a smart card, a digital versatile disc (DVD), a CD-ROM, a solid state hard drive, an optical disk, a magneto-optical disk, and a register file of the processor. Examples of optical disks include Compact Disks (CD) and Digital Versatile Disks (DVD), for example CD-ROM, CD-RW, CD-R, DVD-ROM, DVD-RW, or DVD-R disks. Various storage media may be fixed within the processor 130 or may be transportable, such that the one or more programs stored thereon can be loaded into the processor 130 so as to implement various aspects of the present teachings discussed herein.

Input/output (I/O) circuitry 108 controls communication to elements and devices external to the control unit 106. The I/O circuitry 108 acts as an interface including necessary logic to interpret input and output signals or data to/from the processor 130. The I/O circuitry 108 is configured to receive the acquired live image from the image acquisition device 102, for example, via a wired or wireless connection. The I/O circuitry 108 is also configured to receive preoperative images of the anatomical object T from the pre-operative contour signature database 134, and provide potential contour signature matches of the anatomical object T determined in the control unit 106 to the display 104.

The surgical system 100 comprises a user interface 110. The user interface 110, like the display 104 are illustratively coupled to the control unit 106 via a hardware interface (not shown) and the I/O circuitry 108 as would be appreciated by those skilled in the art. The hardware interface enables the processor 130 to interact with various components of the surgical system 100, as well as control an external computing device (not shown) and/or apparatus. The hardware interface may allow the processor 130 to send control signals or instructions to various components of the surgical system 100, as well as an external computing device and/or apparatus. The hardware interface may also enable the processor 130 to exchange data with various components of the surgical system, as well as with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

The user interface 110 allows the clinician to interact with surgical system 100 through a computer or computer system (not shown). The user interface 110 comprises, for example, a touch screen, a keyboard, a mouse, a trackball or touchpad. Generally, the user interface 110 may provide information or data to the clinician and/or receive information or data from the clinician. The user interface 110 may be configured to receive input from the clinician to be received by the computer, and may provide output to the user from the computer. In other words, and as will become clearer as the present description continues, the user interface 110 may be configured to enable the operator to control or manipulate the computer, and the user interface 110 may be configured to allow the computer to indicate the effects of the clinician's control or manipulation. The display of data or information on the display 104 or a graphical user interface thereof, is an example of providing information to the clinician. The receiving of data through a touch screen, keyboard, mouse, trackball, touchpad, pointing stick, graphics tablet, joystick, gamepad, webcam, headset, gear sticks, steering wheel, wired glove, wireless remote control, and accelerometer are all examples of components of the user interface 110, which enable the receiving of information or data from an operator.

The processor 130 is configured to process the preoperative images of the anatomical object T from one or more orientations to generate the pre-operative contour signature database 134 of preoperative contour signatures of the anatomical object T. The processor 130 is configured to process the acquired live image to generate a real-time contour signature of the anatomical object T.

In accordance with a representative embodiment, the processor 130 is configured to perform contour signature-based registration. The contour signature-based registration comprises generation of a contour signature for both preoperative and intraoperative (real-time) portions of the particular medical or surgical procedure. As described more fully below, contour signature generation, used as part of a registration procedure of a representative embodiment, includes the extraction of a silhouette. The camera view is a maximum-area 2D projection of the 3D organ, so the silhouette of the anatomical object represents its contour at the viewed orientation. This produces a sampling of points that define the contour.

Next, contour signature generation includes re-sampling of the points to the highest resolution. Notably, points along the defined contour may be spaced unevenly due to varying curvature, so interpolation may be performed between the sample points at the highest resolution possible so that the result is a comparatively smooth contour that can be scaled. This interpolation using one or more known interpolation techniques by the processor 130 through specific programs generated for that purpose and stored in memory 132.

Next, contour signature generation includes determining a signature as local curvature along the contour. There are various ways that a signature can be computed from a given (re-sampled) contour, so long as the result identifies the organ/object at the viewed orientation. The present description may focus on contour signatures that capture the physical shape of the organ, but other encoding schemes are possible.

No matter what method that is selected, the contour signature generation is carried out by the processor 130 using images gathered from the image acquisition device 102, the pre-operative contour signature database 134 of preoperative contour signatures of the anatomical object T, and by execution of the relevant programs (instructions) stored in memory 132. Ultimately, the processor 130 generates the contour signature generation by computing a signature as local curvature along the contour.

An example of a physical contour signature is a local curvature. Local curvature will have a lower value at straight segments and higher values at curved segments, commensurate with the degree of curvature. The local curvature $s_i$ along the contour at a point i can be computed as the cross product of vectors extending from the point position $p_i$ to adjacent points along the contour to either side; these vectors are denoted $v_-$ and $v_+$. This computation is shown in the equations below, where c is a parameter that can be tuned to skip adjacent points in the event that the samples are noisy.

$$v_- = p_i - p_{i-c}$$

$$v_+ = p_{i+c} - p_i$$

$$s_i = |v_- \times v_+| / |v_-| \|v_+\|$$

The processor 130 compares the real-time contour signature to the pre-operative contour signature database 134 of preoperative contour signatures of the anatomical object T to generate a match automatically, or generate a group of potential contour signature matches, and transmits the real-time contour signature and the group of potential contour signature matches to the display 104 for selection of a final contour signature match by a user, as will be described in further detail below. The processor 130 registers the image acquisition device 102 to the surgical site S based upon an orientation corresponding to the selected final contour signature match.

As illustrated, the processor 130 may include a memory 132 that includes storage of a pre-operative contour signature database 134. Such memory 132 may also include or have access to a non-transitory computer readable medium as will be described below.

So, the pre-operative contour signature database 134 is generated preoperatively by collecting individual pre-operative contour signatures. In a representative embodiment, these pre-operative contour signatures may be of a CT image over a range of 3D orientations. Generally, the pre-operative contour signatures are generated by the processor 130 based upon preoperative images that may include 3D images such as those obtained via computed tomography (CT), ultrasound, magnetic resonance imaging (MRI), positron emission tomography (PET), single-photon emission computed tomography (SPECT) etc.

A CT scan makes use of computer-processed combinations of many X-ray images taken from different angles to produce cross-sectional (tomographic) images (virtual 'slices') of specific areas of a scanned object, allowing the user to see inside the object without cutting. Digital geometry processing is used to generate a three-dimensional image of the inside of the object from a large series of two-dimensional radiographic images taken around a single axis of rotation. CT produces a volume of data that can be manipulated in order to demonstrate various bodily structures based on their ability to block the X-ray beam. Although, typically, the images are generated in the axial or transverse plane, and this volume of data can be reformatted in various planes or even as volumetric (3D) representations of structures.

In the present illustrative approach, virtually rotating the CT image is equivalent to varying the camera view orientation, so the pre-operative contour signature database 134 contains possible signatures that could be found via the image acquisition device 102 (e.g. an endoscope) during the real-time part of registration. This functionality depends on the equivalency between contours generated from the CT (preoperative) and endoscopy (real-time), which is considered to be a fair and usable assumption.

The generation of the pre-operative contour signature database 134 according to a representative embodiment is described in connection with FIGS. 2A-2C.

Figures 2A, 2B:
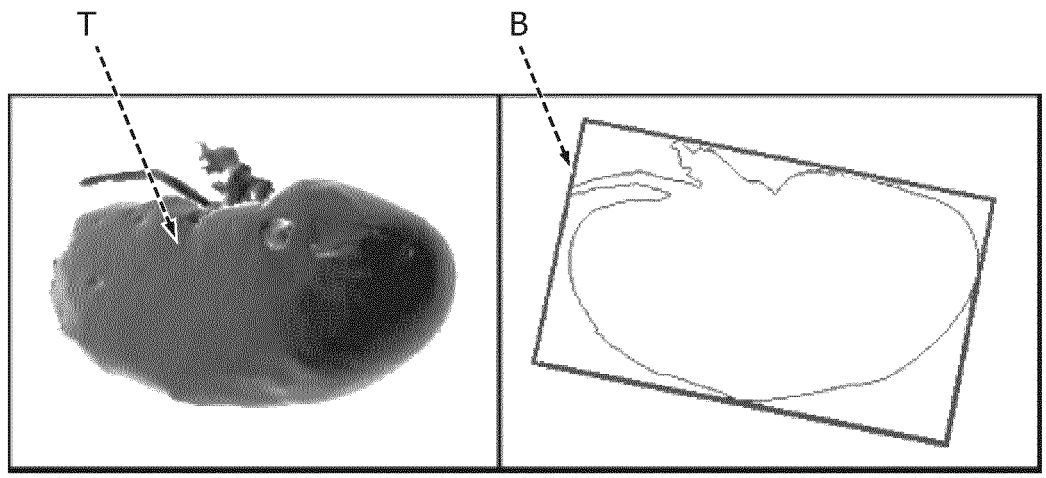
FIG. 2A is an intraoperative (or live) image of an anatomical object used in the surgical system of FIG. 1.
FIG. 2B is a contour of the anatomical object in FIG. 2A.

In FIG. 2A, a CT (pre-operative) image of a kidney at a particular known orientation is shown. Notably, the use of a kidney as the anatomical target T is merely illustrative, and is in no way limiting of the present teachings.

In FIG. 2B, a corresponding contour is extracted from the silhouette of the kidney, wherein the rectangular outline B may also be computed to speed up a subsequent matching process.

Figure 2C:
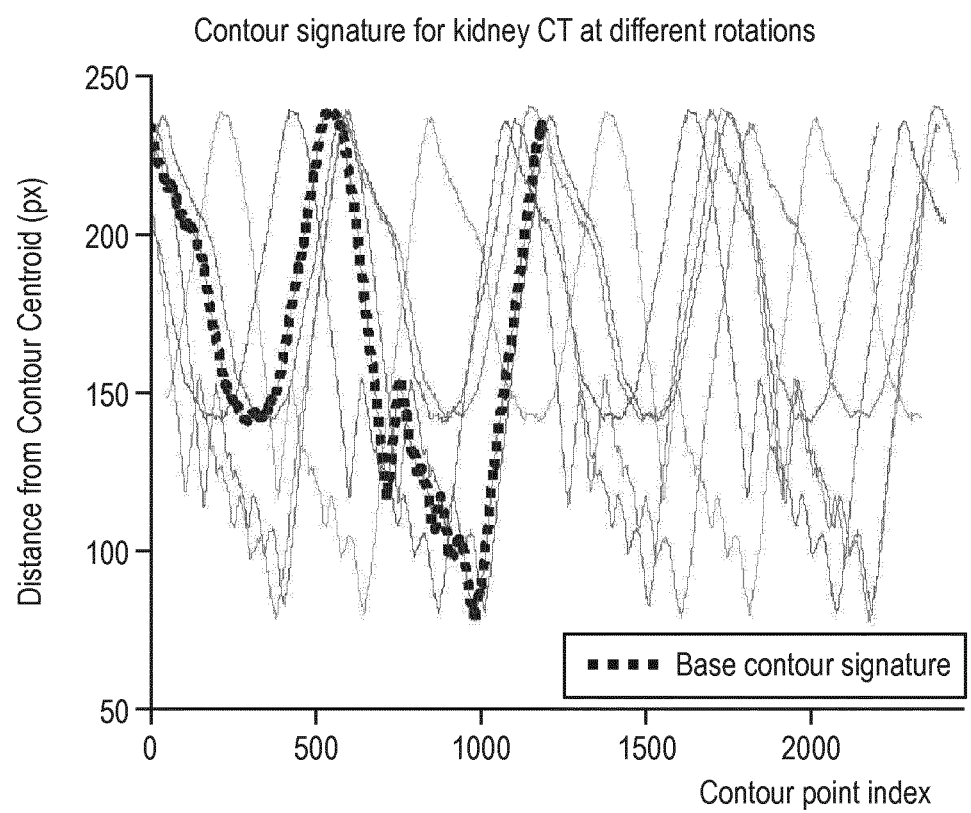
FIG. 2C is a pre-operative contour signature of the anatomical object generated based upon images from a preoperative image acquisition device.

In FIG. 2C, a collection of contour signatures from a series of CT orientations of the kidney is shown in the graph. This collection of contour signatures forms the pre-operative contour signature database 134 for this particular anatomical target. This represents the pre-operative contour signature database 134. Furthermore, the computed outline (rectangular or any other shape) can be included in the pre-operative contour signature database 134.

Since the orientation that generates each signature from the CT volume is known, finding the best match between a real-time generated signature and one in the pre-operative contour signature database 134 yields the corresponding orientation of the image acquisition device 102 or endoscope, and thus the registration, as will be discussed in further detail below.

In a representative embodiment, contour signatures are computed using interoperative images captured by the image acquisition device 102, which is illustratively an endoscope. Under live endoscopy, a camera snapshot or still image is used to generate a single, real-time contour signature CS. Generation of such a single, real-time contour signature can be carried out using a method similar to the one used to generate the pre-operative contour signature database 134 as described more fully above. However, segmentation of the contour may be more challenging due to the presence of other objects in the environment or surgical site S. As such, a more sophisticated approach known in art can perform automated or semi-automated segmentation, or the organ contour (or some subset thereof) can be manually drawn in software using a conventional computer mouse, pen mouse, touchscreen, or other input device (e.g., user interface 110).

After the single live contour signature is gathered, cross-correlation between the live image and the contour signatures in the pre-operative contour signature database 134 is carried out algorithmically by the processor 130, using specific programs for this purpose stored in memory 132. For example, the single live contour signature CS may be matched against the precompiled pre-operative contour signature database 134 by the processor. One benefit of the technique of the presently described method of a representative embodiment over known registration methods is realized. To this end, the problem of registering a 3D object to a 2D projection of the same object, a potentially time-consuming effort in the absence of external localization systems, is reduced to a comparatively fast 1D cross-correlation against a list of signals. The process may be further accelerated by excluding from the search of the pre-operative contour signature database 134 for orientations that are clearly not matching, as determined by computation of the rectangular box show in FIG. 2B. The method of the present representative embodiment shown for computing such a box uses principle component analysis of the organ shape, but other techniques are contemplated by the present teachings. For example, other shape descriptors realized using known methods such as spherical harmonic shape modeling techniques, and Reeb graphs are contemplated for use in the present teachings.

Figure 3:
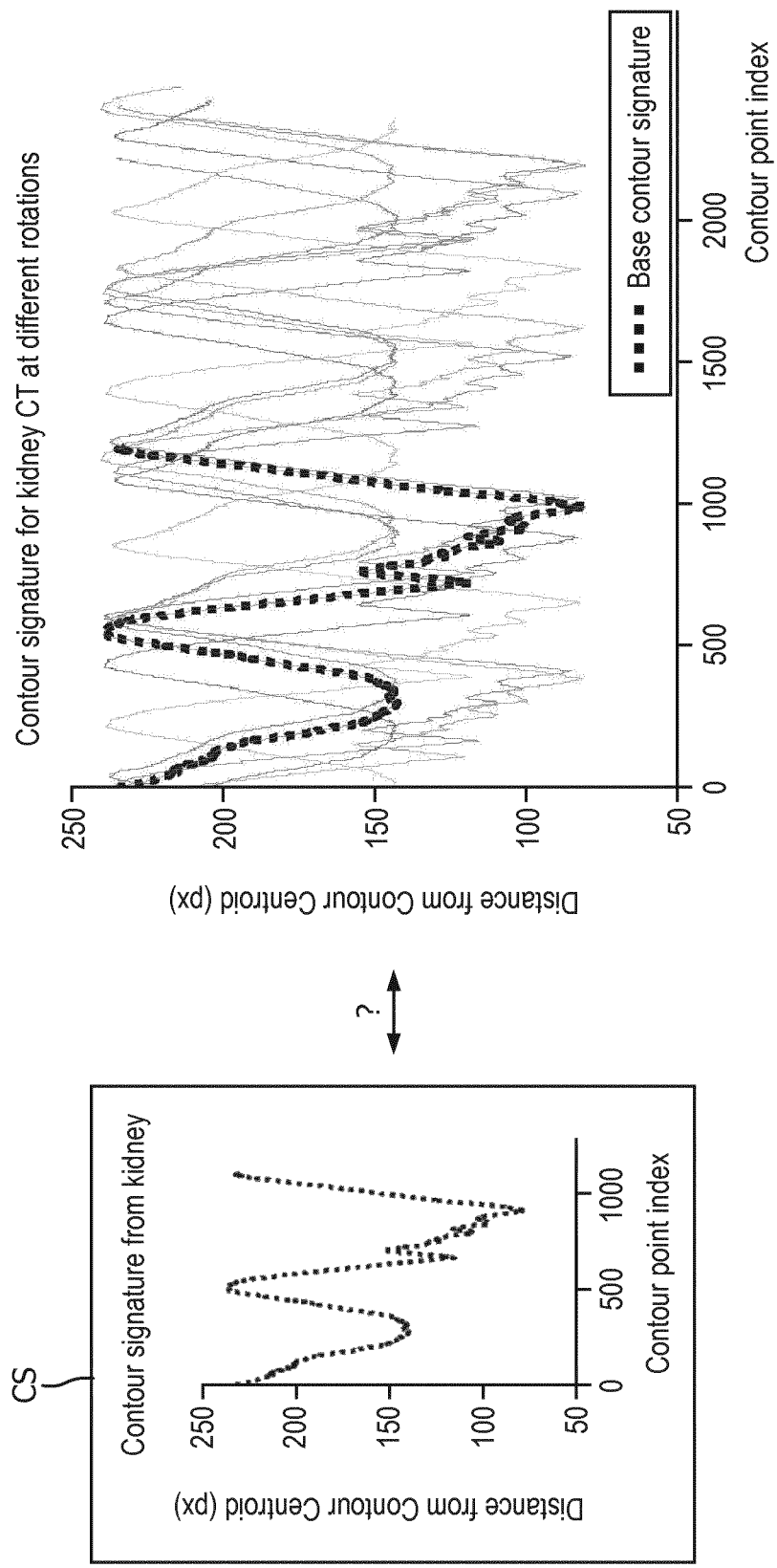
FIG. 3 is a schematic illustration of the comparison of the live contour signature generated from the contour in FIG. 2B and the pre-operative contour signature of the anatomical object of FIG. 2C.

FIG. 3 illustrates the matching process of a representative embodiment, in which a real-time contour signature CS is generated from an image from the image acquisition device 102 (e.g., an endoscopic image) that is compared by the processor 130 to the images stored in the pre-operative contour signature database 134 of preoperative contour signatures generated from CT using cross-correlation.

The processor 130 using specific programs from memory 132 determined the best match of the live image to those stored in the pre-operative contour signature database 134 based upon the best matches, for example by achieving a predefined certainty. Alternatively, the best N matches found in the previous step as determined by the cross-correlation distance metric can be presented to a user for final selection. In other words, the live image and the best N matches may be displayed on the display 104.

Figure 4:
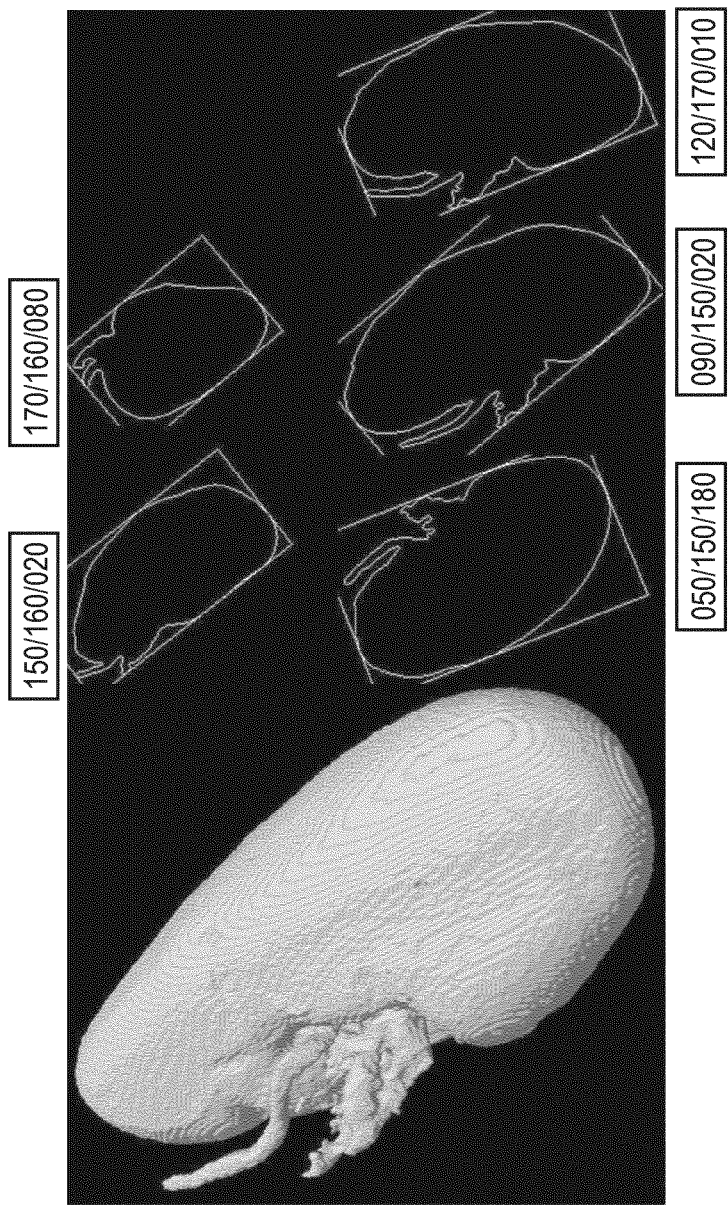
FIG. 4 is a schematic representation of an example of a live image of the anatomical object displayed with the five best matching contours juxtaposed.

FIG. 4 shows an example of a live image displayed with the five best matching contours juxtaposed. After selection by a clinician, the corresponding orientation is used to register the endoscope and CT images.

Figure 5:
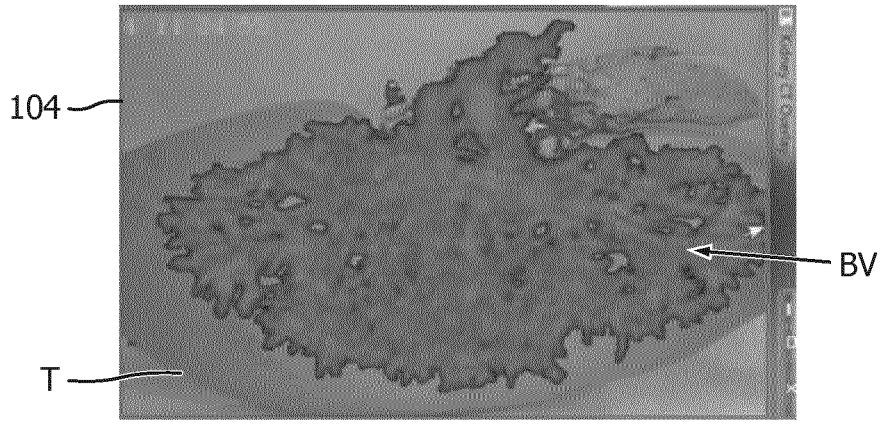
FIG. 5 shows an overlay of blood vessels on a live image of a kidney (i.e. anatomical object) on the display in the surgical system of FIG. 1.

Once the registration is complete, the CT image can be overlaid on the endoscopic video to provide the clinician with anatomical, contextual information, as illustrated in FIG. 5, for example, which shows an overlay of blood vessels BV on a live image of a kidney (i.e. anatomical object T) on the display 104.

Registration can be maintained by repeating the earlier steps can be automatically, or be carried out on-demand whenever the endoscope is repositioned.

In certain embodiments, the processor 130 may be further configured to process a selection signal from a user interface 110 for selection of the final contour signature match by the user. In other words, as the live image and the best 5 matches may be displayed on the display 104 shown in FIG. 4, the surgeon or clinician may then choose the best match, for example, via a user interface 110. In certain embodiments, the processor 130 may be further configured to process an activation signal from the user interface 110 to activate a registration mode.

In certain embodiments, the processor 130 may be further configured to augment live images from the image acquisition device 102 with preoperative images, for example, as shown in FIG. 5.

In certain embodiments, the processor 130 may be further configured to process the acquired live image to generate the real-time contour signature of the anatomical object T using segments or portions of the contour of the anatomical object T.

Figure 6:
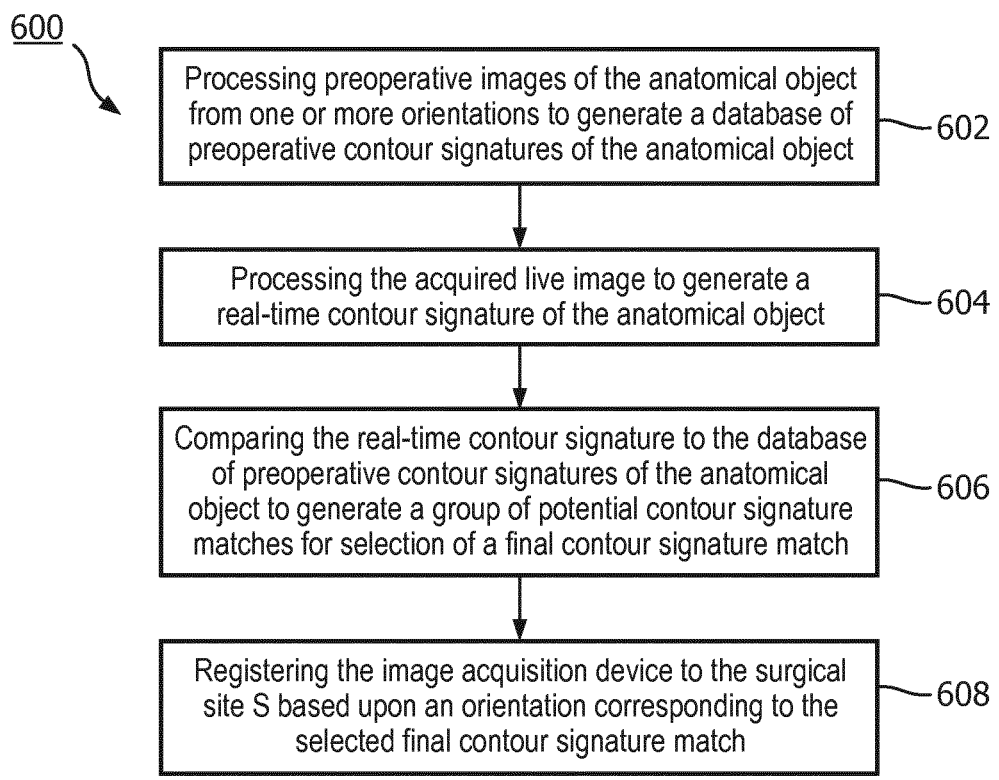
FIG. 6 is a flowchart illustrating various steps in a method to register the image acquisition device to the surgical site in accordance with features of an embodiment of the present invention.

Further details of a method 600 in accordance with features of the present approach are discussed with additional reference to the schematic diagram of FIG. 6. Embodiments of the invention may also be directed to a non-transitory computer-readable storage medium stored in memory 132, and having stored therein machine readable instructions configured to be executed by a processor 130 to control the surgical system 100 including the image acquisition device 102 configured to acquire a live image of the anatomical object T at the surgical site S. Using the machine readable instructions, the processor 130 performs a method 600 to register the image acquisition device 102 to the surgical site S. The method includes: 602 processing pre-operative images of the anatomical object from one or more orientations to generate the pre-operative contour signature database 134 of the anatomical object T; 604 processing the acquired live image to generate a real-time contour signature of the anatomical object T; 606 comparing the real-time contour signature to the pre-operative contour signature database 134 of preoperative contour signatures of the anatomical object to generate a group of potential contour signature matches for selection of a final contour signature match; and 608 registering the image acquisition device 102 to the surgical site S based upon an orientation corresponding to the selected final contour signature match.

In certain embodiments, the method may further comprise transmitting the real-time contour signature and the group of potential contour signature matches to a display 104 for selection of the final contour signature match by a user or clinician.

In certain embodiments, the method may further comprise processing a selection signal from a user interface 110 for selection of the final contour signature match by the user. The method may further comprise processing an activation signal from the user interface 110 to activate a registration mode.

In certain embodiments, the method may further comprise augmenting live images from the image acquisition device 102 with the preoperative images.

In certain embodiments, the method may further comprise processing the acquired live image to generate the real-time contour signature of the anatomical object T using segments of a contour of the anatomical object T.

In certain embodiments, the method may further comprise comparing the real-time contour signature to the pre-operative contour signature database 134 of preoperative contour signatures of the anatomical object T to generate the group of potential contour signature matches includes the exclusion of some preoperative contour signatures based upon a shape of the anatomical object, for example, as discussed above with reference to FIG. 2B.

The present approach is part of a technological progression towards smart systems and devices. Possible applications of real-time registration between live endoscopy and preoperative images (e.g. CT images) include: augmented reality of live video with preoperative CT, surgical navigation (especially in minimally invasive surgery where the workspace is obscured from view), and finding anatomical targets and tumors.

While this disclosure describes contour signature based registration in the context of endoscopic procedures, the method is applicable to procedures using other imaging (e.g., ultrasound) or shape sensing (e.g., optical shape sensing, infrared range sensing) modalities as well. Furthermore, these alternative modalities may not provide a dense set of features for matching that is often found in endoscopy, increasing the significance of contour signatures for registering images, devices, and anatomy in a computer-assisted surgical intervention.

In view of this disclosure it is noted that the various semiconductor structures and active semiconductor devices can be implemented in a variety of materials and variant structures. Further, the various materials, structures and parameters are included by way of example only and not in any limiting sense. In view of this disclosure, those skilled in the art can implement the present teachings in determining their own applications and needed materials and equipment to implement these applications, while remaining within the scope of the appended claims.

What is claimed is:

1. An apparatus for registration of an image acquisition device, the apparatus comprising:
a processor configured to:
receive preoperative images of an anatomical object captured at a plurality of orientations;
generate a database of preoperative contour signatures of the anatomical object from the preoperative images, wherein each preoperative contour signature is generated based on degree of curvature of segments along a contour of the anatomical object viewed at an orientation of the plurality of orientations;
generate a real-time contour signature of the anatomical object from a live image;
compare the real-time contour signature to the database of preoperative contour signatures of the anatomical object to generate a group of potential contour signature matches for selection of a final contour signature match; and
register the image acquisition device to a surgical site based upon an orientation corresponding to the selected final contour signature match.

2. The apparatus according to claim 1, further comprising input/output (I/O) circuitry comprising:
a first input configured to receive the live image from the image acquisition device;
a second input configured to receive the preoperative images of the anatomical object from the image acquisition device;
a first output configured to provide the potential contour signature matches to a display; and
a second output configured to provide live images of the surgical site from the image acquisition device to the display.

3. The apparatus according to claim 1, wherein the processor is further configured to transmit the real-time contour signature and the group of potential contour signature matches to a display for selection of the final contour signature match by a user.

4. The apparatus according to claim 3, wherein the processor is further configured to process a selection signal from a user interface for selection of the final contour signature match by the user.

5. The apparatus according to claim 1, wherein the processor is further configured to process an activation signal from a user interface to activate a registration mode.

6. The apparatus according to claim 1, wherein the processor is further configured to augment live images from the image acquisition device with the preoperative images.

7. The apparatus according to claim 1, wherein the processor is further configured to process the live image to generate the real-time contour signature of the anatomical object using segments of a contour of the anatomical object.

8. The apparatus according to claim 1, wherein the processor is further configured to compare the real-time contour signature to the database of preoperative contour signatures of the anatomical object to generate the group of potential contour signature matches based upon a shape of the anatomical object.

9. A surgical system comprising:
an image acquisition device configured to acquire a live image of an anatomical object at a surgical site;
a display configured to display live images of the surgical site;
a controller comprising:
input/output (I/O) circuitry configured to receive the acquired live image from the image acquisition device, receive preoperative images of the anatomical object captured at a plurality of orientations from the image acquisition device, and provide potential contour signature matches of the anatomical object to the display; and
a processor configured to:
generate a database of preoperative contour signatures of the anatomical object from the preoperative images, wherein each preoperative contour signature is generated based on degree of curvature of segments along a contour of the anatomical object viewed at an orientation of the plurality of orientations;
generate a real-time contour signature of the anatomical object from the acquired live image;
compare the real-time contour signature to the database of preoperative contour signatures of the anatomical object to generate a group of potential contour signature matches;
transmit the real-time contour signature and the group of potential contour signature matches to the display for selection of a final contour signature match by a user; and
register the image acquisition device to the surgical site based upon an orientation corresponding to the selected final contour signature match.

10. The surgical system according to claim 9, wherein the display comprises:
a first display configured to display the live images of the surgical site; and
a second display configured to display the real-time contour signature and the group of potential contour signature matches for selection of the final contour signature match by the user.

11. The surgical system according to claim 10, wherein the I/O circuitry comprises:

a first input configured to receive the live images from the image acquisition device;
a second input configured to receive the preoperative images of the anatomical object from the image acquisition device;
a first output configured to provide the real-time contour signature and the group of potential contour signature matches to the second display; and
a second output configured to provide the live images of the surgical site from the image acquisition device to the first display.

12. The surgical system according to claim 9, further comprising a user interface; wherein the processor is further configured to process a selection signal from the user interface for selection of the final contour signature match by the user.

13. The surgical system according to claim 9, further comprising a user interface; wherein the processor is further configured to process an activation signal from the user interface to activate a registration mode.

14. The surgical system according to claim 9, wherein the processor is further configured to augment the live images from the image acquisition device with the preoperative images.

15. The surgical system according to claim 9, wherein the processor is further configured to process the acquired live image to generate the real-time contour signature of the anatomical object using segments of a contour of the anatomical object.

16. The surgical system according to claim 9, wherein the processor is further configured to compare the real-time contour signature to the database of preoperative contour signatures of the anatomical object to generate the group of potential contour signature matches based upon a shape of the anatomical object.

17. A non-transitory computer-readable storage medium having stored therein machine readable instructions to control a surgical system, the machine readable instructions, when executed by a processor, cause the processor to:
receive preoperative images of an anatomical object captured at a plurality of orientations;
generate a database of preoperative contour signatures of the anatomical object from preoperative images, wherein each preoperative contour signature is generated based on degree of curvature of segments along a contour of the anatomical object viewed at an orientation of the plurality of orientations;
generate a real-time contour signature of the anatomical object from an acquired live image;
compare the real-time contour signature to the database of preoperative contour signatures of the anatomical object to generate a group of potential contour signature matches for selection of a final contour signature match; and
register an image acquisition device to a surgical site based upon an orientation corresponding to the selected final contour signature match.

18. The non-transitory computer-readable storage medium according to claim 17, wherein the machine readable instructions, when executed by the processor, further cause the processor to: transmit the real-time contour signature and the group of potential contour signature matches to a display for selection of the final contour signature match by a user.

19. The non-transitory computer-readable storage medium according to claim 18, wherein the machine readable instructions, when executed by the processor, further cause the processor to: process a selection signal from a user interface for selection of the final contour signature match by the user.

20. The non-transitory computer-readable storage medium according to claim 17, wherein the machine readable instructions, when executed by the processor, further cause the processor to: process an activation signal from a user interface to activate a registration mode.

21. The non-transitory computer-readable storage medium according to claim 17, wherein the machine readable instructions, when executed by the processor, further cause the processor to: augment live images from the image acquisition device with the preoperative images.

22. The non-transitory computer-readable storage medium according to claim 17, wherein the machine readable instructions, when executed by the processor, further cause the processor to: process the acquired live image to generate the real-time contour signature of the anatomical object using segments of a contour of the anatomical object.

23. The non-transitory computer-readable storage medium according to claim 17, wherein the machine readable instructions, when executed by the processor, further cause the processor to: compare the real-time contour signature to the database of preoperative contour signatures of the anatomical object to generate the group of potential contour signature matches based upon a shape of the anatomical object.

\* \* \* \* \*